United States Patent [19]

Schwartz et al.

[11] 4,444,792
[45] * Apr. 24, 1984

[54] FERMENTATION OF WHEY TO PRODUCE A THICKENING POLYMER

[75] Inventors: Robert D. Schwartz, Concord; Elizabeth A. Bodie, El Cerrito, both of Calif.

[73] Assignee: Stauffer Chemical Company, Westport, Conn.

[*] Notice: The portion of the term of this patent subsequent to Aug. 16, 2000 has been disclaimed.

[21] Appl. No.: 284,422

[22] Filed: Jul. 20, 1981

[51] Int. Cl.³ .................. A23C 21/02; C12P 19/06; C12R 1/64

[52] U.S. Cl. .................................. 426/41; 426/43; 435/104; 435/910

[58] Field of Search .............. 435/104, 245, 253, 910; 426/41, 43

[56] References Cited

U.S. PATENT DOCUMENTS 3,343,962  9/1967  Peer .......................... 435/253 X
3,455,786  7/1969  Miescher ..................... 435/910 X
3,497,359  2/1970  Peer ........................... 435/41 X

OTHER PUBLICATIONS

Stauffer et al., Extracellular Microbial Polysaccharide Production by Fermentation on Whey or Hydrolyzed Whey, Journal of Food Science, vol. 43, 1978, (pp. 756-758).

Manual for Dairy Manufacturing Short Courses, Litho in U.S.A., Kurtz Bros., Clearfield, Pa. 1956, (pp. 56-57).

Primary Examiner—David M. Nafe
Attorney, Agent, or Firm—Michael J. Bradley

[57] ABSTRACT

Diary whey, a waste product of cheese production, is fermented with *Xanthomonas campestris* ATTCC 31923 to produce a fermented whey product containing a thickening polymer. The fermented whey product can be used as a thickening agent by the food industry. Yeast extract may be added to the whey prior to fermentation. *Xanthomonas campestris* ATCC 31923 is a novel microorganism having the ability to grow on lactose as the sole source of carbon.

7 Claims, 3 Drawing Figures

FIGURE I
X. CAMPESTRIS ATCC-31923 FERMENTATION IN WHEY MEDIUM
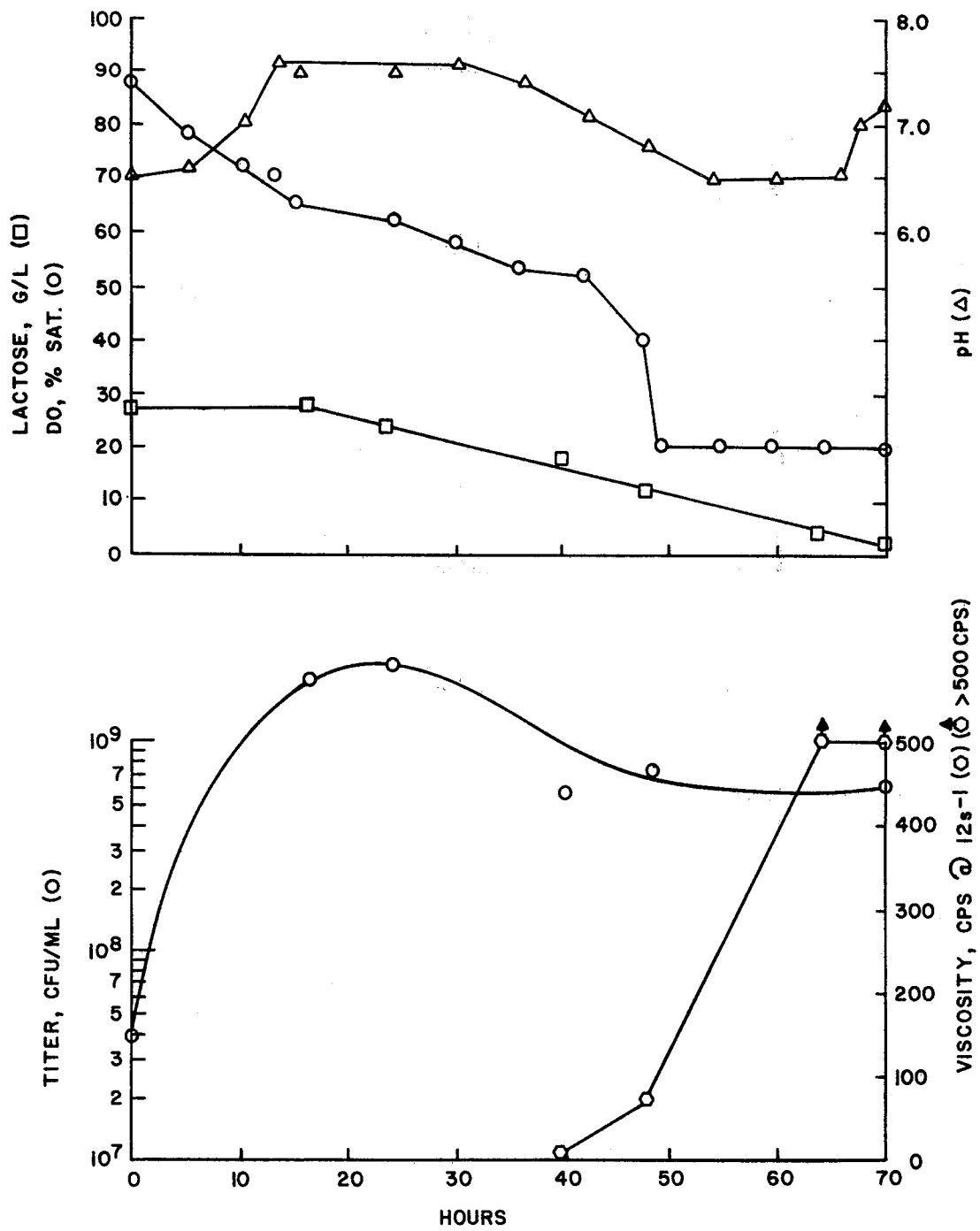

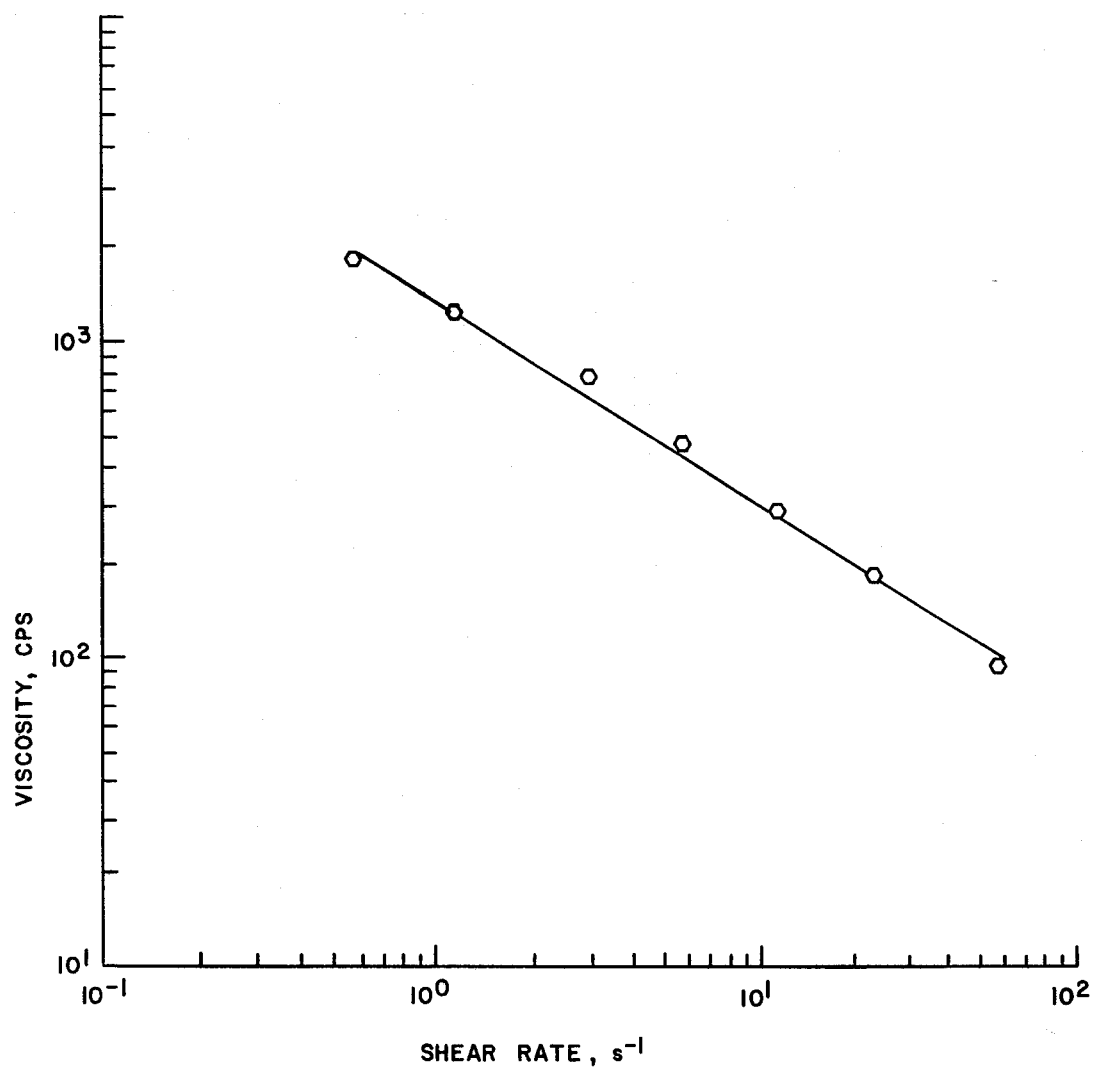
FIGURE II
VISCOSITY VS. SHEAR RATE CURVE FOR DRIED FUNCTIONALIZED WHEY

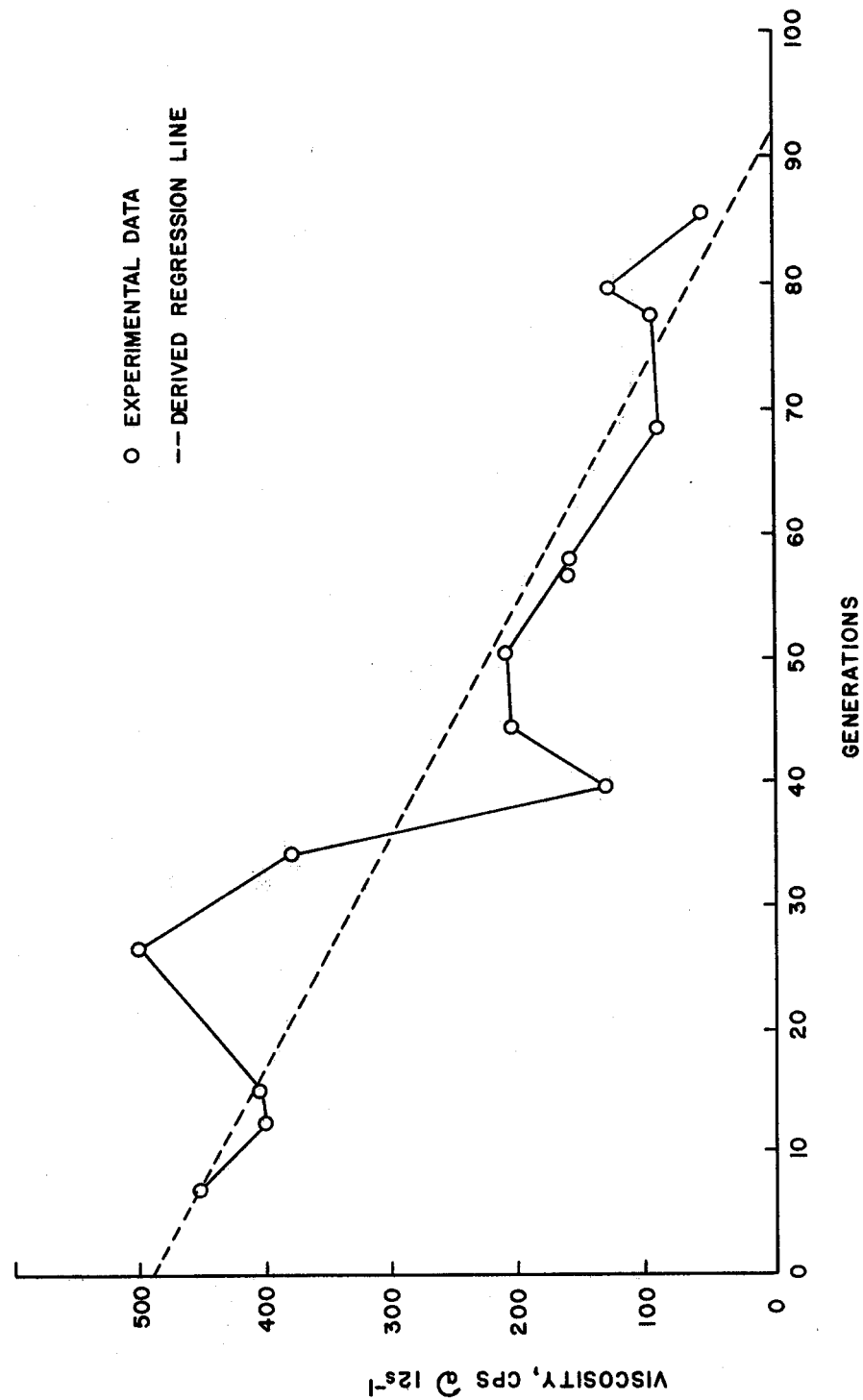
FIGURE III
REGRESSION ANALYSIS OF VISCOSITY VS. NO. GENERATIONS ATCC-31923 IN TEKLAC MEDIUM

FERMENTATION OF WHEY TO PRODUCE A THICKENING POLYMER

BRIEF DESCRIPTION OF THE INVENTION

The process of this invention provides a method for functionalizing whey by forming a fermentation broth of the whey and yeast extract and then fermenting this whey broth with the novel organism *Xanthomonas campestris* BB-1L (ATCC 31923).

BACKGROUND OF THE INVENTION

Controlled fermentation of foods can be used as a means of improving functionality of the foods. Dairy whey, a food, may be an economical source of a fermentable substrate, and is widely used as an accepted milk-derived ingredient in manufactured foods. If whey can be properly functionalized by fermentation with an organism that produces a thickening polymer when grown on the whey substrate, it is possible to obtain whey products that may serve the function of a stabilizer, thickener, emulsifier, or flavor enhancer.

Whey is the fluid medium containing a very low concentration of milk solids and a high concentration of lactose. Disposal of this waste by-product by drying is an energy-intensive, expensive procedure which results in an expensive by-product, while sewering of the whey is prohibitive in cost due to the high biological oxygen demand which is placed on municipal sewer systems.

The most desirable method of handling this waste stream is to produce a high quality natural food ingredient from the whey waste product. Applicant has discovered a novel method of producing a functionalized whey product for use as a food ingredient or any type of product where milk solids and lactose are acceptable ingredients.

DESCRIPTION OF THE DRAWINGS

FIG. I shows a graph of a typical fermentation of *Xanthomonas campestris* ATCC 31923 in a medium containing 4% Teklack (whey), and 0.05% yeast extract.

FIG. II shows a viscosity versus shear rate curve for a typical dried functionalized whey produced by the fermentation techniques of this invention.

FIG. III shows a graph of a regression analysis of viscosity v. number of generations ATCC 31923 was grown in whey medium.

DETAILED DESCRIPTION OF THE INVENTION

A functionalized dairy whey product having a viscosity greater than 200 centipoise at a $12s^{-1}$ sheer rate for use as a food ingredient that may serve as a stabilizer, thickener, or emulsifier, can be produced by fermenting a mixture comprising whey, optionally yeast extract and a pH buffer with the novel organism *Xanthomonas campestris* ATCC 31923 to produce a functionalized whey product containing a thickening polymer produced by the novel organism *Xanthomonas campestris* ATCC 31923.

DERIVATION OF XANTHOMONAS CAMPESTRIS ATCC 31923

*X. campestris* ATCC 31923 was isolated for its ability to grow on lactose as sole source of carbon and energy. It was derived from *X. campestris* BB-1 (ATCC 31922) following several serial passages in lactose minimal medium containing 1.5% lactose, 0.5% $K_2HPO_4$, 0.2% $NH_4Cl$, 0.1% NaCl, 0.01% $MgSO_4$, and 0.01% yeast extract. In this medium, at about 28° C., ATCC 31923 has a generation time of about three hours, viable cell titers of about $10^9$/ml or greater are reached, the lactose in the medium is metabolized, and the broth does not become viscous.

When *X. campestris* ATCC 31923 was subsequently grown in whey medium containing 2% Teklac, 0.25% $K_2HPO_4$, 0.01% yeast extract at about 28° C., the generation time was about three hours, viable titers, of about $10^9$ cells/ml or greater were reached, the lactose in the medium was metabolized, and the broth became viscous.

Although it is known in the art that an ultra-filtered and hydrolyzed whey medium fermented with *Xanthomonas campestris* results in excellent polymer formation, all growth to date on unhydrolyzed whey has failed to result in polymer production; see, K. R. Stauffer and J. G. Leeder, 1978, *J. Food Sci.*, 43: 756-758, "Extracellular Microbial Polysaccharide Production by Fermentation on Whey or Hyrolyzed Whey," and M. Charles and M. K. Radjai, 1977 "Xanthan Gum From Acid Whey" in *Extracullular Microbial Polysaccharides*, eds. P. A. Sandford and A. I. Laskin. ACS Symp. Ser. No. 45, pp. 27-39. Fermentation using ATCC 31923 of a whey broth comprising unhdyrolzed whey (acid or sweet), and optionally yeast extract results in polymer formation and functionalization of the whey so that the whey product can be utilized as a food ingredient. This aerobic fermentation can be carried out preferably in a pH range of 6 to 8, preferably with the pH maintained in a range from about 6.5 to about 7.5. The fermentation can be carried out at a temperature from about 20° to 35° C., preferably carried out at a temperature from about 25° to about 30° C. Typical composition of Teklac (sweet dairy whey) is as follows:

| CHEMICAL AND PHYSICAL SPECIFICATIONS | |
| --- | --- |
| Ingredient Listing: Whey | |
| Typical Proximate Analysis | |
| Protein (N × 6.38) % | 12.7 |
| Fat % | 1.1 (1.25% Maximum) |
| Moisture % | 4.5 (5.0% Maximum) |
| Ash % | 8.0 |
| Lactose % | 71.3 |
| Calories, Cal/100 g | 350.0 |
| Typical Vitamin & Mineral Analysis | |
| Vitamin A I.U./100 g | Nil |
| Vitamin C mg/100 g | Nil |
| Thiamin mg/100 g | 0.40 |
| Riboflavin mg/100 g | 1.76 |
| Niacin mg/100 g | 1.00 |
| Calcium % | 0.71 |
| Iron % | Nil |
| Vitamin $B_{12}$ ug/100 g | 2.12 |
| Phosphorus % | 0.69 |
| Pantothenic Acid mg/100 g | 4.09 |
| Microbiological Standards | |
| Standard Plate Count | 10,000/g (Maximum) |
| Coliforms | 9/g (Maximum) |
| E. coli | Negative |
| Salmonella | Negative |

The nutritional values listed above are within 80% of the value declared in compliance with Federal Nutritional Regulations 21 CFR §1.17(4)(ii).

|                              | Typical Range   | Limit       |
| ---------------------------- | --------------- | ----------- |
| Solubility Index             | 0.1–0.5 ml      | 1.25 ml Max.|
| Acidity                      | 0.10–0.14%      | 0.16 Max.   |
| Alkalinity of Ash            | 175–200 ml      | 225 ml Max. |
| Scorched Particles           | 7.5 mg          | 15.0 mg Max.|
| Particle size (Through 40 Mesh) | 99–100%      | 98% Min.    |

Concentration of whey can range from about 0.5% to about 12.0%, preferably 2% to 4%. The additional yeast in the fermentation broth can range from about 0 to about 0.5%, preferably from about 0.01% to about 0.1%. Adequate fermentation broth viscosities (>200 cps and preferably >800 cps at a $12s^{-1}$ shear rate) are usually reached within 48 to 72 hours. All of the above weight percents are in weight per volume.

*X. campestris* ATCC 31923 was isolated by continuous enrichment and selection in a lactose minimal medium from the parent strain, ATCC 31922, which either grows poorly or not at all, the produces little or no polymer, when lactose is the sole source of carbon and energy. Further, ATCC 31922 grows well but does not produce polymer on whey medium without glucose supplementation, and the lactose in the whey is not used.

To ensure the ability of ATCC 31923 to grow and produce polymer in whey medium the strain in routinely maintained in lactose minimal medium during storage and inocula production. When polymer production is desired a lactose minimal medium grown culture is transferred to whey medium. Prolonged maintenance in whey results in the loss of the ability of ATCC 31923 to produce viscous broths in whey indicating a reversion to preferential growth on protein.

EXAMPLE 1

FIG. 1 shows a graph of a typical fermentation of *Xanthomonas campestris* ATCC 31923 in a medium containing 4.0% Teklac and 0.05% yeast extract. The medium was sterilized by autoclaving at 15 pounds per square inch (psi) for 15 minutes. The fermentation was conducted in a fermentor to which air was pumped at the rate of 1 volume/volume/min, agitation was at the rate of 500 rpm, and the dissolved oxygen concentration maintained at a minimum of 20% saturation. A Bioflow ® fermentor was used (New Brunswick Scientific Co., N.J.). The initial pH was about 6.5 and was controlled between 6.5 and 7.5. The inoculum was 3% volume/volume from a lactose minimal medium grown culture. The figure shows the general increase in viscosity over time, growth of the organism, and the initial increase in pH, followed by a decrease in pH, typical of this fermentation, and a decrease in lactose concentration.

The high viscosity broths produced by fermentation techniques of this invention may be dried and/or sterilized by autoclave plus lyophilization, spray drying, or other techniques.

EXAMPLE 2

A viscosity versus shear rate curve for a typical dried functionalized whey so produced is shown in FIG. II. The sample was tested on a 2.5 XLVT Wells-Brookfield microviscometer having a 3° cone at 25° C. The sample size was 2.0 milliliters. The sample consisted of a 1% solution (weight/vol) of functionalized whey in deionized water. The pH was 7.0 and lactose concentration was 2.6 grams per liter. The increase in viscosity with decrease in shear rate is typical of pseudoplastic polymers.

EXAMPLE 3

Prolonged maintenance in whey results in the loss of the ability of ATCC 31923 to induce viscous broths in whey. ATCC 31923 was serially transferred (2% vol/vol) at 48 hour intervals, in Teklac medium, for a total of 85 generations. The medium contained 2% Tekac, 0.25% $K_2HPO_4$, 0.1% yeast extract. At the time of transfer the viscosity was measured and the culture titered on YM agar (Difco, Detroit, Mich.).

The results are shown in Table I. For the first 35 generations (5 transfers) the broth viscosity remained high at about 400 cps. For the next 45 generations (8 transfers) the viscosity dropped to 100–200 cps. A regression analysis of the viscosity v generation number is shown in FIG. III. The reversion frequency (loss of ability to produce high viscosity broths in Teklac medium) is such that for at least about 55 generations broths with viscosities >200 cps are produced. However, continued transfer in whey eventually resulted in loss of the abiity to produce viscous broths.

TABLE I

*X. Campestris* ATCC 31923 Stability. Growth and polymer production in 2% Teklac, 0.25% $K_2HPO_4$, 0.1% yeast extract.

| Transfer Number | Titers, cfu/ml 0 hours | Titers, cfu/ml 48 hours | Generations per transfer | Generations cumulative | Viscosity cps @ 12 $s^-$ @ 48 h |
| --- | --- | --- | --- | --- | --- |
| 1  | $1.8 \times 10^7$ | $2.6 \times 10^9$ | 7.2  | 7.2  | 453 |
| 2  | $3.5 \times 10^7$ | $2.5 \times 10^9$ | 6.2  | 13.4 | 398 |
| 3  | $1.0 \times 10^7$ | $4.0 \times 10^7$ | 2.0  | 15.4 | 402 |
| 4  | $2.0 \times 10^5$ | $7.9 \times 10^8$ | 11.9 | 27.3 | >480 |
| 5  | $1.4 \times 10^7$ | $3.0 \times 10^9$ | 7.8  | 35.1 | 378 |
| 6  | $6.0 \times 10^7$ | $2.1 \times 10^9$ | 5.1  | 40.2 | 129 |
| 7  | $4.2 \times 10^7$ (cal) | $1.0 \times 10^9$ | 4.6  | 44.8 | 206 |
| 8  | $1.2 \times 10^7$ | $1.0 \times 10^9$ | 6.4  | 51.2 | 208 |
| 9  | $1.5 \times 10^7$ | $1.0 \times 10^9$ | 6.1  | 57.3 | 161 |
| 10 | $1.9 \times 10^7$ | $4.7 \times 10^7$ | 1.3  | 58.6 | 158 |
| 11 | $1.0 \times 10^5$ | $1.3 \times 10^8$ | 10.4 | 69.0 | 91 |
| 12 | $2.6 \times 10^6$ (cal) | $1.1 \times 10^9$ | 8.8  | 77.8 | 95 |
| 13 | $3.7 \times 10^7$ | $2.0 \times 10^8$ | 2.4  | 80.2 | 129 |
| 14 | $6.0 \times 16^6$ (cal) | $3.0 \times 10^8$ | 5.6  | 85.8 | 58 | cfu/ml = colony forming units/ml.

The functionalized whey product of this invention can be used as a food ingredient where milk solids and/or whey, and/or thickeners, and/or stabilizers are used such as in ince cream, salad dressing, foam stabilizer (meringue), puddings, snack foods, etc.

What is claimed is:

1. A process for producing a functionalized dairy whey product comprising the steps of:
   (a) forming a fermentation broth consisting essentially of unhdyrolyzed whey containing unhydrolyzed lactose and
   (b) fermenting the broth with the organism *Xanthomonas campestris* ATCC 31923 to produce a functionalized dairy whey product containing a thickening polymer produced by the organism.

2. The process of claim 1 wherein the concentration of the whey is from about 0.5% to about 12% weight per volume and yeast extract is added to the whey in an amount up to about 0.5% weight per volume.

3. The process of claim 2 wherein the yeast extract concentration is from 0.01 to 0.1% weight per volume.

4. The process of claim 1 wherein the fermentation is conducted at a temperature of from about 20° to about 35° C.

5. The process of claim 1 wherein the fermentation is conducted at a temperature of from about 20° to about 35° C. and the pH is maintained in a range of from about 6 to about 8.

6. The process of claim 1 plus the additional step:
(c) drying said functionalized whey product to form a dry functionalized whey product.

7. A biologically pure culture of the organism *Xanthomonas campestris* ATCC 31923 having the ability to grow on lactose as the sole source of carbon and energy.

* * * * *